United States Patent
Groß

(10) Patent No.: US 8,740,257 B2
(45) Date of Patent: Jun. 3, 2014

(54) FLUID CONNECTOR COMPONENT COMPRISING SEVERAL PLUGGABLE ELEMENTS

(71) Applicant: Erbe Elektromedizin GMBH, Tübingen (DE)

(72) Inventor: Stefan Groß, Tubingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 0 days.

(21) Appl. No.: 13/774,343

(22) Filed: Feb. 22, 2013

(65) Prior Publication Data

US 2013/0214527 A1 Aug. 22, 2013

(30) Foreign Application Priority Data

Feb. 22, 2012 (EP) .................................... 12156560

(51) Int. Cl.
*F16L 39/00* (2006.01)
(52) U.S. Cl.
USPC .................. 285/124.2; 285/124.1; 285/124.4; 285/123.6; 285/123.12
(58) Field of Classification Search
USPC ............. 285/124.1, 124.2, 124.3, 124.4, 325, 285/326, 123.12, 123.5
See application file for complete search history.

(56) References Cited

U.S. PATENT DOCUMENTS

| | | | | |
|---|---|---|---|---|
| 1,973,610 A | * | 9/1934 | Connors | 285/124.1 |
| 2,086,424 A | | 7/1937 | Koehler | |
| 3,214,195 A | | 10/1965 | Zahuranec et al. | |
| 3,337,181 A | | 8/1967 | Wennerstrom | |
| 3,469,863 A | * | 9/1969 | Riester et al. | 285/124.4 |
| 3,508,580 A | | 4/1970 | Snyder | |
| 3,937,496 A | | 2/1976 | Zahid | |
| 4,269,219 A | * | 5/1981 | Dybvig | 285/124.1 |
| 5,297,820 A | * | 3/1994 | Martin | 285/124.2 |
| 6,860,516 B2 | * | 3/2005 | Ouchi et al. | 285/124.1 |
| 7,175,207 B2 | * | 2/2007 | Prochiner | 285/124.1 |
| 7,299,823 B2 | * | 11/2007 | Smith | 285/124.1 |
| 7,464,967 B2 | * | 12/2008 | Mieger et al. | 285/124.1 |
| 8,517,428 B2 | * | 8/2013 | Langenfeld et al. | 285/124.1 |
| 2010/0181764 A1 | | 7/2010 | Imoto | |

FOREIGN PATENT DOCUMENTS

| | | |
|---|---|---|
| GB | 2419647 | 5/2006 |
| WO | WO2007118334 | 10/2007 |
| WO | WO2008142672 | 11/2008 |

* cited by examiner

*Primary Examiner* — David E Bochna
(74) *Attorney, Agent, or Firm* — Dickstein Shapiro LLP

(57) ABSTRACT

A fluid connector including pluggable elements, for example in the form of connector pins or connector sockets that are supported so as to be movable in a direction transverse to a joining direction. Resilient element may be disposed for pre-specifying a rest position of the corresponding pluggable elements.

14 Claims, 2 Drawing Sheets

FLUID CONNECTOR COMPONENT COMPRISING SEVERAL PLUGGABLE ELEMENTS

CROSS-REFERENCE TO RELATED APPLICATIONS

The present application claims priority under 35 U.S.C. §119(a) to European Patent Application No. EP 12 15 6560.0, filed Feb. 22, 2012, the disclosure of which is incorporated by reference in its entirety.

TECHNICAL FIELD

Embodiments of the invention relate to a fluid connector component with pluggable elements for receiving or dispensing fluids, particularly, for medical apparatuses or instruments.

BACKGROUND

In the practice of medicine, many instruments are used that require different fluid (i.e. gaseous or liquid) media, for example, compressed gases, water, or the like. In order to supply the fluid to the instruments, the instruments are connected by way of a fluid connector to an appropriate medical apparatus that provides the fluids in the desired state and in the desired quantity. In doing so, the fluids may be under considerable pressure, which is the case in cryosurgical applications. In a still relatively simple case, the appropriately pressurized cryogenic fluid must be supplied to the instrument, and the depressurized cryogenic fluid must be carried away. To accomplish this, two separate fluid lines are required. In many cases, a third fluid line for the additional return of the cryogenic fluid is required, for example when the freezing process was interrupted and the thawing process is to be accelerated. In this case, it is possible to add additional fluid lines for fluids that are required for the treatment process.

SUMMARY

It is the object of the disclosed embodiments to provide a connector component which can be used for connecting several fluid channels between a medical apparatus and a medical instrument so that the connector components used are easy to actuate and are reliably sealed.

The fluid connector component in accordance with the disclosed embodiments includes at least two pluggable elements that, for example, may be configured as a connector socket or as a connector pin. Combinations of connector sockets and connector pins on one connector component are also possible. Both pluggable elements of a connector component may be oriented so as to be parallel with respect to each other and thus define a common joining direction. In one embodiment, they are at a distance from each other in a direction transverse to this joining direction. If more than two pluggable elements are provided, they may be arranged in one line in transverse direction so that they form a straight row. These pluggable elements may also deviate from this line and thus be arranged, for example, in the form of a triangle, a circle, a square, a zigzag line, a rectangle, a trapezoid, a star, or they may be distributed otherwise. The two pluggable elements may also be configured so as to be asymmetrical. In doing so, it can be ensured that the allocation of the male connector and the female connector are defined clearly enough to allow only one single allocation and orientation for joining them together.

In one embodiment, the second pluggable element is configured as a female connector. In this embodiment, it may have a cylindrical female connector opening that represents an insertion space for a male connector pin. In this case, the insertion space may be expanded in a funnel-like manner on its open end in order to act as an insertion guide. The female connector may be substantially rotationally-symmetrical with the exception of minor deviations, for example, fluid channels, radial bores, and the like.

The female connector may be made of metal or a dimensionally stable plastic material. If the female connector is made of metal, it may be provided, partially or fully, with a coating, for example, a PTFE coating, to reduce corrosion and friction and, in doing so, reduce pushing and pulling forces.

In another embodiment, the pluggable element is a male connector pin. In this embodiment, it is also desirable for the male connector pin to be rotationally-symmetrical (with the exception of minimal deviations, for example, fluid channels, radial bores, and the like). In this case, the pluggable element has an essentially cylindrical shell surface and an optionally conical face. On its shell surface, it may be provided with two or more sealing elements that are at an axial distance from each other. A fluid channel may terminate between two sealing elements on the shell surface, the fluid channel then communicating with a fluid feed or removal line.

If corresponding fluid connector components that include male connector pins and female connector sockets are joined together, the sealing elements of the male connector pin establish a fluid-tight connection between the male connector pin and the female connector socket. The sealing elements are elastic in the radial direction in order to perform their sealing function. Due to the additional transverse movability of at least one of the pluggable elements, i.e., the male connector pin and/or the female connector socket, the male connector pin and the female connector socket will concentrically come into alignment with each other when they are joined, so that the sealing elements active between the male connector pin and the female connector socket will be uniformly stressed along their entire circumference. In doing so, a lasting, good seal of this type of connector connections can be created and gasket wear can be reduced from repeated connection and disconnection. In addition, this reduces the manual force required to insert the male fluid connectors into the female fluid connectors or remove the male fluid connectors therefrom.

Furthermore, fluid connectors according to a disclosed embodiment include a large number of individual channels. Male connectors and female connectors that are not individually paired, i.e., not specifically adapted to each other, can be brought into engagement with each other. The wear on the sealing elements is minimized, e.g., the wear of the connector pins. The pushing and pulling forces are relatively small, even in non-paired male fluid connectors and female fluid connectors. Also, due to the concentric alignment of the male connector pin and the female connector socket, it can be ensured that uniform flow conditions exist at all times and that there will be no flow vortices or cavitation due to maladjustments.

Due to the small pushing and pulling forces, it is also possible to provide the operator with a haptic feedback regarding the proper insertion of the male connector. To accomplish this, a detent device may be provided, for example. It can be distinctly felt when the detent device snaps in because the relatively minimal pushing forces do not override the forces occurring when the detent device snaps in. The detent device may consist of one or more snap hooks and of one or more associate detent recesses that are provided on the fluid connector components.

Furthermore, a cover cap may be movably supported against a fluid connector component that is configured as a male connector. This cover cap may comprise transversely movable female connectors for closing the connector pins. The connector pins may also display transverse movability. In this case, the receiving openings of the cover cap for receiving the connector pins on the cover cap may be rigidly arranged. In most instances, a cover cap is necessary in the processing and sterilizing of medical instruments. The cover cap may also be connected to the male connector via a snapping mechanism.

In order to provide the aforementioned advantages, in one embodiment, only a few of the pluggable elements are supported so as to movable. However, in another embodiment, all the pluggable elements of the respective fluid connector component are supported so as to be movable in at least one transverse direction. For example, all the pluggable elements may be supported so as to be movable toward and away from each other. It is also possible to support one pluggable element so as to be movable in a first transverse direction and another pluggable element so as to be movable in a second transverse direction that is different from the first transverse direction.

At least a few of the pluggable elements are disposed to be movable toward and away from each other. It is also possible to support one, a few or all of the pluggable elements so as to be movable in the radial directions.

It is possible to support the pluggable elements in a freely movable manner, i.e., with a certain lateral play. However, it is desirable that resilient element be provided to retain the pluggable element in a rest position at, for example, a center position. For resilient support, it is possible to use one or two resilient elements, for example, in the form of tubular or annular elastomer elements. The elastomer elements may be prefabricated elements having a poreless or foamed body. They may also be elastomer elements that are produced by having a shapeless compound penetrate into the appropriate spaces of the fluid connector component and by hardening the material. The elastomer elements may have a solid body or a body with at least one hollow space. They may be configured as O-rings, elastomer hose sections bent to form a ring, hose sections placed in a helical line, or any other resilient element.

In one embodiment, the movably supported pluggable elements are enclosed by a gas conveying sleeve that is supported so as to be movable together with the pluggable elements. In one embodiment, the resilient element supports the gas conveying sleeve. Interposed between the gas conveying sleeve and the female connector, there may be sealing elements that retain the gas conveying sleeve and the female connector concentrically with respect to each other and delimit a gas conveying space. In one embodiment, the gas conveying space is an annular space or a space having the form of an annular gap, sealed toward the outside. In addition, it may be connected—via at least one channel—with a line leading away from (or to) a fluid connector component. Furthermore, the gas conveying space is connected with the female connector opening via one or more radial bores.

The resiliency constant of the sealing elements active between the female connector and the gas conveying sleeve is desirably greater than the resiliency constant of the resilient element. Correspondingly, the yield of the resilient elements is clearly greater than the yield of the sealing elements. As a result of this, when the male connector pin is being inserted in the female connector socket and a lateral shift of the female connector socket occurs, the resilient elements are deformed but not the gaskets.

BRIEF DESCRIPTION OF DRAWINGS

Additional details of exemplary embodiments are explained in greater detail below, with reference to the drawings, in which.

DETAILED DESCRIPTION

Figure 1:
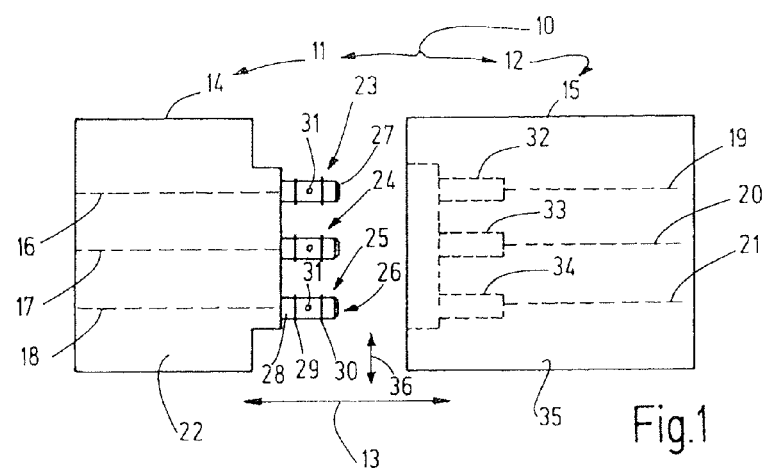
FIG. 1 shows a schematic general representation of a fluid connector comprising two fluid connector components.

FIG. 1 shows a fluid connector 10 that comprises two connector components 11, 12 that may be joined or pulled apart in a joining direction 13. In one embodiment, the connector component 11 is configured as a male connector 14, and the connector component 12 is configured as a female fluid connector 15.

In one embodiment, the male fluid connector 14 is associated with a medical instrument, for example a cryotechnical instrument, that comprises a total of three fluid channels 16, 17, 18, which are disposed to supply and remove liquid or gaseous fluids. The fluid channels 16, 17, 18 continue via tubular or hose-like lines to the distal end of the instrument, which is not illustrated in FIG. 1.

In operation, the fluid channels 16, 17, 18 communicate with the fluid channels 19, 20, 21, which may be connected to sources or sinks for the fluids and leading to the female fluid connector 15.

The male fluid connector 14 includes a male connector housing 22 from which project two or more, for example three, connector pins 23, 24, 25 in joining direction 13. In one embodiment, all of the connector pins 23, 24, 25 may be configured to be the same. However, they may also have different dimensions, for example different lengths and/or different cross-sections or diameters, in order to allow joining the male fluid connector 14 to the female fluid connector 15 in only one selected single position. The connector pins 23, 24, 25 may be arranged at equal relative distances on a straight line or, in order to avoid any mix-up, be arranged at unequal distances or also not in a straight line but, e.g., in the form of a triangle or the arc of a circle. The cross-sections of the connector pins 23, 24, 25 may have a circular cross-section. It is also possible to use different cross-sectional forms.

Independent of size and dimensions, each connector pin 23, 24, 25 has a base body that may be essentially shaped like a circular cylinder. On its face; there may be provided an insertion guide 26, for example shaped in the form of a conical surface 27 (see also FIG. 5). Furthermore, each connector pin 23, 24, 25 has on its cylindrical circumferential surface 28 two sealing elements 29, 30, such as gasket rings, e.g., O-rings, between which a fluid opening 31 is provided, which communicates with a fluid channel 16. This applies equally to all the other connector pins 23, 24 and fluid channels 17, 18.

The connector pins 23, 24, 25 are allocated to connector sockets 32, 33, 34 as are shown in dashed lines in FIG. 1. The connector pins 23, 24, 25 and the connector sockets 32, 33, 34 are generally referred to herein as "pluggable elements."

Figure 2:
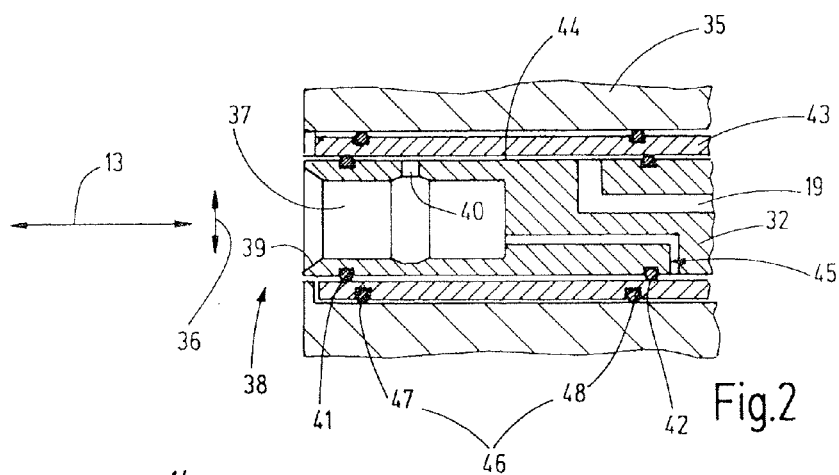
FIG. 2 shows a schematized detail, vertically in section, of a connector component configured as a female connector component.

FIG. 2 shows the connector socket 32 as an example and as also representing the two other connector sockets 33, 34. At least one, of the connector sockets 32, 33, 34 is movably supported in a connector body of a housing 35 of the female fluid connector 15 so as to be movable in a transverse direction. This may also referred to as a "floating" support. To do so, the connector socket 32 displays limited movability in a first transverse direction 36 that extends transversely to the joining direction 13 and that extends toward and/or away from the adjacent connector socket 33. In one embodiment, at least one or more or all of the connector sockets 32, 33, 34 may be supported so as to be movable in another transverse direction, e.g., in any other radial direction. In the present exemplary embodiment, the connector sockets 32, 33, 34 are supported so as to be uniformly movable in all the radial directions.

The connector socket 32 has a female connector opening 37 that essentially represents a blind hole. The cross-section of each female connector opening 37 is adapted so as to match the cross-section of the respectively allocated connector pin 23, 24, 25. On its open end, the female connector opening 37 may be provided with an insertion guide 28 in the form of a conical surface 39. Other than that, the female connector opening 37 is, in one embodiment, essentially cylindrical. At one point that is on the same level as the fluid opening 31 when the connector pin 32 is inserted, one or more radial bores 40 may be provided.

It is desirable to provide two sealing elements 41, 42 on the cylindrical outside circumference of the connector socket 32. In one embodiment, the sealing elements 41, 42 are sealing rings, e.g., O-rings, at an axial distance from each other. The sealing elements 41, 42 may be seated, e.g., in axially spaced apart annular groves of the connector socket 32. The fluid channel 19 terminating at the circumferential surface of the connector socket 32 branches off between the sealing elements 41, 42.

The connector socket 32 is accommodated in a gas conveying sleeve 43 that may be configured, e.g., as a straight tubular piece. The inside circumferential surface of the gas conveying sleeve 43 abuts against the sealing elements 41, 42 of the connector socket 32, e.g., the O-rings. With the connector socket 32, the gas conveying sleeve 43 delimits a gas conveying space 44 that communicates with the fluid channel 19 and the radial bore 40. Another channel 45 terminates on the bottom in the female connector opening 37 and connects the opening with the annular gap formed between the connector socket 32 and the gas conveying sleeve 43, but outside the gas conveying space 44. This channel 45 is disposed to remove displaced fluids such as air, when the connector pin 23 is inserted into the female connector opening 37.

The unit consisting of the female connector socket 32 and the gas conveying sleeve 43 is arranged in the housing 35 in a corresponding receptacle so as to be movable, at least in one transverse direction 36, however overall radially, e.g., with play. In order to avoid an undefined position and thus to accomplish the resilient centering of the female connector socket 32, the gas conveying sleeve 43 can also support itself on the housing 35 via at least one or more resilient elements 46. The resilient elements 46 may be may be metal springs, for example in the form of undulated, ring-shaped closed or slit (C-shaped) sheet metal rings or also elements of plastic material, for example in the form of rings, cords or the like. Foamed or solid material may also be used. In the present exemplary embodiment, the resilient elements 46 that are provided are two O-rings 47, 48. However, it is also possible to use a different number of resilient elements 46, in particular O-rings. Regarding their spring action, the resilient elements 46 are disposed to be more resilient than the sealing elements 41, 42 represented, e.g., by the O-rings. In this manner, a lateral displacement of the female connector socket 32 predominantly causes a deformation of the at least one resilient element 56, in which case the gas conveying sleeve 43 and the female connector socket 32 remain centered relative to each other. In this manner, the gas conveying space 44 also remains undeformed, i.e., the gap width of this space having the form of an annular gap is not disadvantageously changed.

The fluid connector 10 described above works as follows:

In the described embodiment, the description of the function assumes that the connector pins 23, 24, 25 are essentially, however not exactly, in alignment with their female connector sockets 32, 33, 34. When the male fluid connector 14 is inserted into the female fluid connector 15, the radially movable female connector sockets 32, 33, 34 will center themselves radially, in that the conical surfaces 27 of the connector pins 23, 24, 25 cooperate with the corresponding conical surfaces 39 of the female connector sockets 32, 33, 34 and thus move the respective female connector sockets 32, 33, 34 in a radial direction. In doing so, the resilient elements 46 are correspondingly deformed. The latter are sufficiently resilient and yield with a minimal application of force. Thus the connector pins 23, 24, 25 can be inserted into the female connector sockets 32, 33, 34 with minimal force. In doing so, the gaskets 29, 30 will center the connector pin 23 in the female connector socket 32. Then, the gaskets 29, 30 are essentially uniformly deformed along their circumference. The same applies to the remaining pairs. The gaskets 29, 30 are considerably less yielding than the resilient elements 46. Like the gaskets 41, 42, the gaskets 29, 30 are also essentially uniformly deformed along their circumference. Therefore, a uniformly good and technically reliable seal is established between the connector pin 23 and the interior wall of the female connector opening 37 along the entire circumference. Also, the gas conveying space 44 is and remains well sealed in a technically reliable manner.

In inserted state, the fluid opening 31 is in alignment with the radial bore 40. Consequently, the fluid channels 16, 19 communicate with each other in an outwardly sealed manner. It is also possible to exchange liquid or gaseous fluids under high pressure between the fluid channels 16, 19 without interference.

Figures 3, 4:
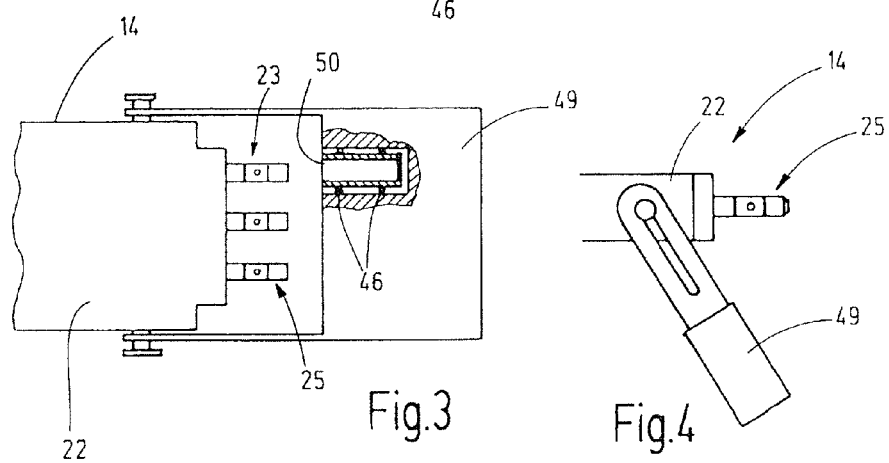
FIG. 3 shows a plan view, partially in section, of a fluid connector component configured as a male connector with a cover cap that is connected to the connector so that the cap cannot be lost.
FIG. 4 shows a side view of the connector of FIG. 3.

As is shown by FIGS. 3 and 4; the male fluid connector 14 may be provided with a cover cap 49, for example, for storage or cleaning purposes, which cap can be held on the male connector housing 22, for example, so the cap 49 cannot be lost. Such a cover cap 49 may comprise dummy sockets 50 acting as female connectors, as is illustrated by the slot allocated to the connector pin 23. The dummy socket 50 can be directly supported by the resilient element 46 on the body of the cover cap 49. Again, the lateral movability of the dummy sockets 50 is suitable to compensate for passible spacing tolerances or other arrangement tolerances of the connector pins 23, 24, 25, and thus allow an easy attachment of the cover cap 49, without damaging or excessively stressing the gaskets 29, 30.

Figure 5:
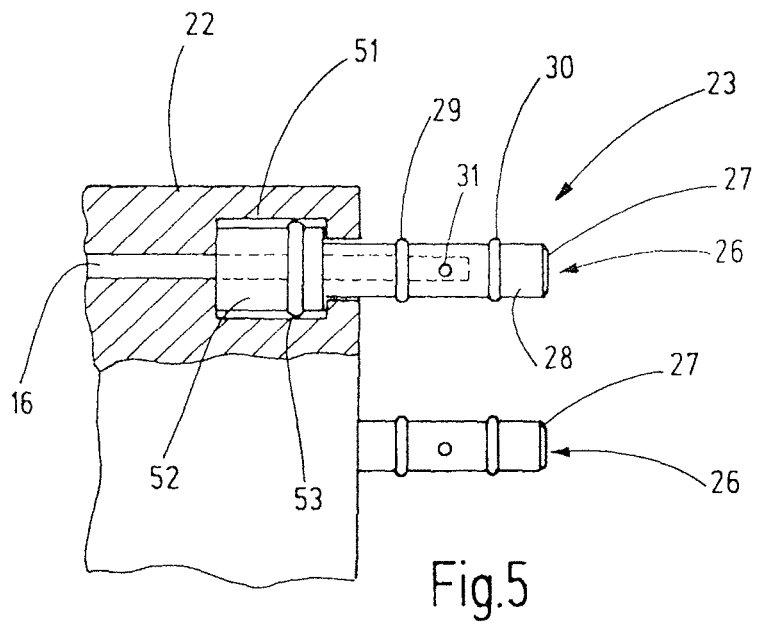
FIG. 5 shows a plan view, partially in section, of details of embodiments of the fluid connector component configured as the male connector.
Figure 6:
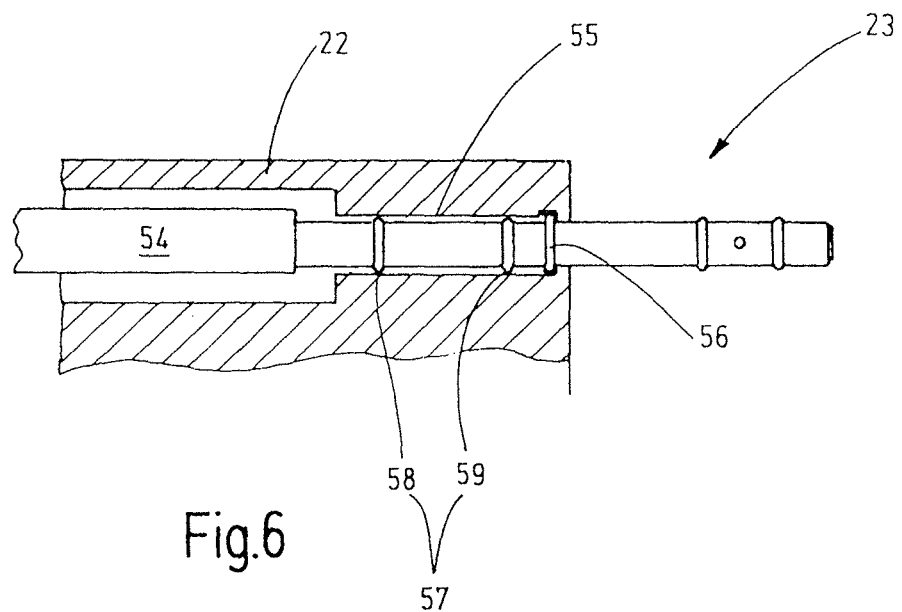
FIG. 6 shows a plan view, partially in section, of details of embodiments of the fluid connector component configured as the male connector.

Referring to the above description, it is assumed that at least two of the female connectors 32, 33, 34 are arranged so as to be radially movable, whereby the radial movability is not restricted by a correspondingly centering spring force of the at least one resilient element 46; however, this is not essential. The spring force caused by the resilient element(s) 46 is lower than the spring force generated by the gaskets 29, 30 or the gaskets 41, 42. In doing so, the connector pins 23, 24, 25 may be rigidly attached to the male connector housing 22. It is also possible to support at least one, more or all of the connector pins 23, 24, 25, so as to be radially movable. FIGS. 5 and 6 show relevant exemplary embodiments.

Referring to FIG. 5, the male connector housing 22 may have a chamber 51 for receiving an end 53 of the connector pin 23. The male connector housing 22 may have a dividing joint (not shown) that extends through the chamber 51 and allows the assembly of the connector pin 23. The connector pin can be held sealed by way of a gasket 53 in the chamber 51. In this case, the gasket 53 acts as a resilient element at the same time. The gasket may be soft enough that it offers an opposing force to a radial movement of the connector pin 23. In one embodiment, the force is substantially smaller than a corresponding force caused by the gaskets 29, 30, with the deformation being the same. The chamber 51 communicates with the fluid channel 16, as is shown in dashed lines in FIG. 5, which extends in an axial direction through the connector pin 23 up to the fluid opening 31.

The embodiment shown in FIG. 6 uses the male fluid connector 23 as the direct connection for a fluid hose 54 that is directly connected by way of a suitable fluid connecting means (not shown) to the proximal end of the connector pin 23. The connector pin 23 extends with radial play through an opening 55 of the male connector housing 22. For axial support, the connector pin 23 may be provided with a collar 56 that is seated with play in a corresponding annular grove of the opening 55, or provided with another suitable axial fastening element. Resilient element 57 may be attached to the connector pin 23, for example in the form of one or two elastomer rings 58, 59. These elastomer rings 58, 59 may be, for example, O-rings. Alternatively, other resilient element may be used.

As in the case of the female connector sockets 32, 33, 34, it is possible to dispense with the resilient element 46, 57, respectively, also in this case. In addition, the resilient element 46, 57 may be replaced by structures of the male connector housing 22 or the housing 35 such as, for example, by a single tab or more tabs of plastic material, by an initially shapeless and subsequently hardening elastomer compound, or the like.

A fluid connector comprises pluggable elements, for example in the form of connector pins 23, 24, 25 or connector sockets 32, 33, 34 that are supported so as to be at least minimally movable in a direction transverse to a joining direction 13. The resilient element 46, 57 may be disposed for pre-specifying a rest position of the corresponding pluggable elements in order to arrange them so as to be movable and without play. This prevents rattling and/or the formation of a visible, irregular, non-concentric arrangement of a connector socket 32 relative to a bore in the housing 35. This non-concentric arrangement could be perceived as being a visual or a quality defect.

What is claimed is:

1. A fluid connector component comprising:
at least two pluggable elements that define a common joining direction,
wherein at least one of the pluggable elements is supported so as to be movable in at least one transverse direction that is oriented transversely to the joining direction,
wherein at least one of the at least two pluggable elements is enclosed by a movably supported gas conveying sleeve, and wherein the gas conveying sleeve is supported against a connector body by at least one resilient element.

2. The fluid connector component of claim 1, wherein the at least two pluggable elements include one of female connector sockets and male connector pins.

3. The fluid connector component of claim 1, wherein the at least two pluggable elements are supported so as to be movable in the at least one transverse direction.

4. The fluid connector component of claim 1, wherein the at least two pluggable elements are supported so as to be movable toward each other and away from each other in the at least one transverse direction.

5. The fluid connector component of claim 1, wherein at least one of the at least two pluggable elements can be moved in all directions that are oriented radially with respect to the joining direction.

6. The fluid connector component of claim 1, wherein the at least two pluggable elements are arranged in a row.

7. The fluid connector component of claim 1, wherein at least one of the at least two pluggable elements is resiliently supported in the at least one transverse direction.

8. The fluid connector component of claim 1, wherein at least one of the at least two pluggable elements comprises a face and an insertion guide on the face.

9. The fluid connector component of claim 8, wherein the insertion guide is defined by a conical surface.

10. The fluid connector component of claim 1, wherein the fluid connector component is for a medical instrument.

11. A fluid connector component comprising:
at least two pluggable elements that define a common joining direction,
wherein at least one of the pluggable elements is supported so as to be movable in at least one transverse direction that is oriented transversely to the joining direction,
wherein at least one of the at least two pluggable elements is enclosed by a movably supported gas conveying, sleeve wherein the gas conveying sleeve is supported against a connector body by at least two resilient elements arranged at a distance from each other.

12. The fluid connector component of claim 11, wherein the at least two resilient elements are ring-shaped elastomer bodies.

13. A fluid connector component comprising:
at least two pluggable elements that define a common joining direction,
wherein at least one of the pluggable elements is supported so as to be movable in at least one transverse direction that is oriented transversely to the joining direction,
wherein at least one of the at least two pluggable elements delimits a gas conveying space by at least two sealing elements that are arranged at a distance from each other in a gas conveying sleeve.

14. The fluid connector component of claim 13, wherein the at least one of the at least two pluggable elements has at least one radial bore that connects the gas conveying space with a female connector opening.

* * * * *

UNITED STATES PATENT AND TRADEMARK OFFICE
CERTIFICATE OF CORRECTION

| | | |
|---|---|---|
| PATENT NO. | : 8,740,257 B2 | Page 1 of 1 |
| APPLICATION NO. | : 13/774343 | |
| DATED | : June 3, 2014 | |
| INVENTOR(S) | : Stefan Groβ | |

It is certified that error appears in the above-identified patent and that said Letters Patent is hereby corrected as shown below:

On the Title Page

The Inventor information in Item (72) should read:

(72) Inventor: Stefan Groβ, Tübingen (DE)

Signed and Sealed this
Seventh Day of October, 2014

Michelle K. Lee
*Deputy Director of the United States Patent and Trademark Office*